United States Patent [19]

Turner

[11] Patent Number: Plant 6,485

[45] Date of Patent: Dec. 27, 1988

[54] ANIGOZANTHOS PLANT NAMED BUSH MAGIC

[75] Inventor: Mervyn L. Turner, Monbulk, Australia

[73] Assignee: Biotech Plants Pty. Ltd., Somersby, Australia

[21] Appl. No.: 33,812

[22] Filed: Apr. 3, 1987

[51] Int. Cl.[4] ..... A01H 5/00

[52] U.S. Cl. ..... Plt./68

[58] Field of Search ..... Plt. 68

*Primary Examiner*—Robert E. Bagwill

*Attorney, Agent, or Firm*—Schwartz, Jeffery, Schwaab, Mack, Blumenthal & Evans

[57] ABSTRACT

A Kangaroo Paw plant (genus Anigozanthos) named Bush Magic having a cream-green inflorescence with suffusions of red-purple hairs and narrow glaucous foliage, spring flowering in warm temperate climate, and superior resistance to Alternaria species.

1 Drawing Sheet

The present invention relates to a new and distinctive cultivar of Kangaroo Paw known by the cultivar name Bush Magic. Kangaroo Paw is the popular name applied to all species of the botanical genera Anigozanthos Labill and Macropidia Harv and their variants and hybrids. Angiozanthos Labill is a genus of eleven described species of herbaceous perennial plants of the family Haemodoraceae, and which are endemic to the south-western region of western Australia. These species, together with the closely allied monotype *Macropidia fuliginosa* (Hook.) Druce, are as above noted jointly referred to by the popular common name Kangaroo Paws.

Wild population of Kangaroo Paws grow in a warm temperate Mediterranean climate (Summer drought). Vitality is at a minimum in late Summer/early Autumn, and some species show or tend to a full deciduous dormancy at this time. Active vegetative growth is reinstated with the onset of lower temperatures and rainfall in the Autumn (Fall). The flowering season varies considerably between species, but the display period is normally of several months somewhere within the range of late Winter to mid-Summer.

Mature plants consist of a clump of leaf fans arising from ramified rhizome which exists at immediate subsurface soil levels. Rhizome extends and branches by annual growth and is more or less persistent. Leaves and roots are replenished on an annual basis.

Leaves arise from rhizome buds and exist as fans of alternate ensheathing leaves arranged on an equitant conduplicate pattern, and with very short internodes.

Individual leaves are normally relatively straight and narrow in length, being approximately parallel sided in the lower half or more, and tapering to an acute point above. As new leaves arise in the center of each fan between the next youngest leaves, older leaves are progressively displaced at an angle. In some species older leaves may become distinctly recurved.

There is variation between species in the stature of leaf fans and in the relative width of individual leaves. In the largest species, leaves may be one meter in length and up to five centimeters wide. In the smallest species, leaves may be ten centimeters in length and one centimeter wide.

The active apical meristem in a leaf fan is located near the base of the fan during the active vegetative growth stage. Eventually, a rapid increase in length of successive internodes occurs accompanied by a decrease in leaf size and followed by a differentiation of the apex, the overall process forming a flower stem. The overall length of the flower stem varies between 1.5 and 2.5 times the length of the basal leaves of the leaf fan according to species.

The inflorescence per se is a unilateral raceme, both series of sub-sessile to shortly pedunculate alternating flowers being oriented in the same direction. Each peduncle is marked by a pointed bract shorter than the flower. The flower is itself bilaterally symmetrical consisting of a spherical tri-locular basal ovary extending into an initially narrower and cylindrical perianth which broadens and flattens and terminates in six lobes. At anthesis the lobes which are contiguous in bud, separate and reflex, the degree varying with species. The style is simple, free, and about as long as the perianth, and terminates in a small sub spherical stigma. The six anthers have short to very short filaments, the points of insertion being towards the apex of the perianth.

Three more or less distinctive patterns in the architecture of the flower stem can be recognized. In some species the architecture is simple, with the stem being simple and terminating in a solitary raceme. In other species, the stem is initially simple but forks immediately sub-terminally, each fork terminating in a raceme. In some species, the stem is initially simple but then branches more or less dichotomously, the node being subtended by a shortened leaf. Secondary branching may occur, but eventually most branches fork, each ultimate branch or fork terminating in a raceme.

In one extreme in some species, the length of the overall flower stem can exceed two meters. At the other extreme, in some species, the stem may rarely be longer than twenty centimeters.

Racemes may be few to many flowered and individual flowers from three centimeters to ten centimeters in length varying with species.

In all species the flowers, and in all but one species the stem, are clothed with a close indumentum of velvet texture. The indumentum is colored and the stem, ovary, and perianth may be distinctively colored. Flower color or pattern of coloration normally applies to that of this indumentum. Development of pigmentation is to some degree a function of environmental conditions, especially of temperature and total irradiance during bud development.

The new cultivar Bush Magic was created by the inventor as a result of a controlled crossing of a selected genotype of the species *Anigozanthos viridis* Endl. (seed parent) with a selected genotype of the species *Anigozanthos onycis* George (pollen parent).

Asexual reproduction by applicant in Monbulk, Victoria, Australia by divisions of the rhizome and by aseptic multiplication of leaf shoots including apical meristem on nutrient media has reproduced the unique features of the new cultivar through successive generations.

The following characteristics distinguish the new cultivar from both its parents and from other Kangaroo Paws known and used in the ornamental horticultural industry.

1. The cultivar exhibits superior resistance compared with either parent to Alternaria species, these air-born fungal species being the major hazard to Kangaroo Paws in cultivation: both parents were themselves selected as genotypes having superior resistance when compared with typical plants within the respective species.

2. The characteristics of Bush Magic are, by and large, intermediate between known cultivars and the two parents. The combination of characteristics emphasizes soft pastel tones and an interesting contrast of foliage and flower color.

3. While the basal leaves of the leaf fan are relatively long and narrow, those of the flower stem are noticeably broader at the base and distinctly curved.

4. While the majority of flower stems are simple and bear a solitary terminal raceme, others are branched or forked. The length of flower stem is typically in the range 40 cm to 50 cm. Each raceme normally produces 12 to 15 flowers.

5. Flowering is normally confined to Spring in warm temperate climatic conditions.

The accompanying colored photographs illustrate the new cultivar, with the colors being as true as it is reasonably possible to obtain in colored reproductions of this type. The photograph at the top is a perspective view of the new cultivar in flower. The bottom photograph is an enlarged photograph of the flower characteristics of Bush Magic.

The following is a detailed description of Bush Magic based on plants grown at Bush Gems Garden Nursery in Monbulk, Victoria, Australia. Color references are made to the Royal Horticultural Society Colour Chart except where general color terms of ordinary dictionary significance are used. Terms used have the same meaning and significance as those used and defined above regarding the characteristics of propagation, plant form, habit of growth, foliage, flowers and rhizome common and general to all plants of Anigozanthos.

Parentage: A hybrid of two selected genotypes of the species *Anigozanthos viridis* Endl. (seed parent) and *Anigozanthos onycis* George (pollen parent).

Propagation: Asexual by (A) Rhizome divisions. Optimum period — late Summer to early Fall. (B) "In vitro" proliferation of multiple shoots from explants of apical meristem with immediate leaf primordia. Five-fold multiplication in four weeks on appropriate media. Rooting in three to five weeks at approximately 20 degrees Celsius root zone temperature in high relative humidity environment. Use of anti-transpirant sprays beneficial.

Plant description:

(A) *Form.*—Clumping, rhizomic, perennial plant suited to cultivation in containers, in gardens (in essentially frost free environments), and as a row-crop cut flower.

(B) *Habit of growth.*—The main period of active growth — rhizome extension, production of new leaf fans, and induction/evocation of flowers — is Winter and Spring. Vegetative growth is slow in Summer even with irrigation.

(C) *Foliage.*—The basal leaves of each leaf fan are of alternate, conduplicate, ensheathing arrangement. (1) Size and shape: Basal leaves up to 25 cm long by 3 mm wide, more or less uniformly tapering to a point (2) Texture: Smooth, glabrous, with a glaucous bloom, scattered hairs along the leaf edges. (3) Color: Mature, healthy foliage is green 139B. The widely spaced leaves of the flower stem decrease from approximately 15 cm in length nearer the base to a few cm near the raceme. The lowermost of these leaves are different in shape than basal leaves, being broader, approximately 10 mm, curved, and displayed in a near horizontal position. Color is the same as basal leaves.

Flowers:

(A) *Flowering habit.*—Flowers in dense, unilateral biseriate racemes, most commonly a single raceme terminal to a simple stem. Typical length of the overall inflorescence is between 40 cm and 50 cm.

(B) *Natural flowering season.*—Spring and early Summer. Young plants produced from tissue culture may have an atypical first flowering season.

(C) *Flower bud.*—More or less uniformly tubular, immediately prior to opening 50 mm to 55 mm in length and approximately 5 mm in diameter. The perianth lobes are fused in a slightly enlarged, asymmetrical tip.

(D) *Flowering raceme.*—Axis straight, the pedicels of the flowers short, approximately 8 mm, spaced at 12 mm intervals, each pedicel subtended by a bract, approximately 15 mm long and 2 mm wide. The lowest flowers of the raceme open first, the perianth lobes reflexing through approximately 150 degrees. buds at the anterior end progressively grow and open. A single raceme typically produces 12 to 15 flowers.

(E) *Individual flower.*—Sub-spherical basal ovary approximately 6 mm diameter, extending into a tubular perianth, approximately 45 to 50 mm in length.

(F) *Color.*—The flower stem is green 141B with a relatively sparse indumentum of hairs of color red-purple 60B. The indumentum of the pedicel ovary is greyed-yellow 161B, but may have a very sparse suffusion of hairs of similar color to the stem indumentum. The color of the indumentum of the perianth is yellow green 145A but towards the tip there is a graduation to an indumentum of color red-purple 60A.

Disease resistance:

Resistance to fungal leaf diseases (viz. Alternaria spp.) is superior to typical wild seedling Kangaroo Paws as confirmed by field trials in various sites and seasons.

I claim:

1. A new and distinct cultivar of Anigozanthos plant named Bush Magic, as described and illustrated, and parts thereof.

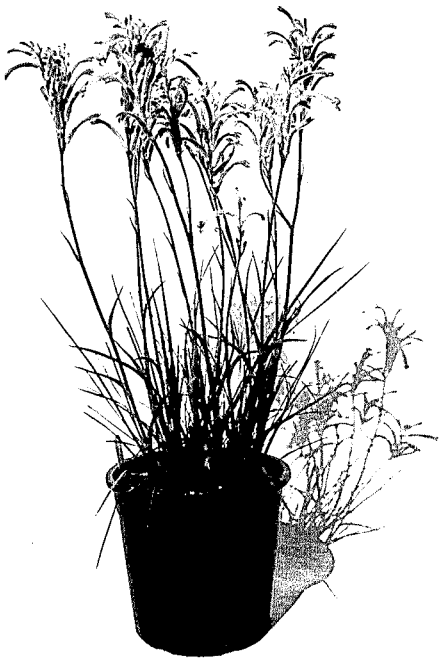
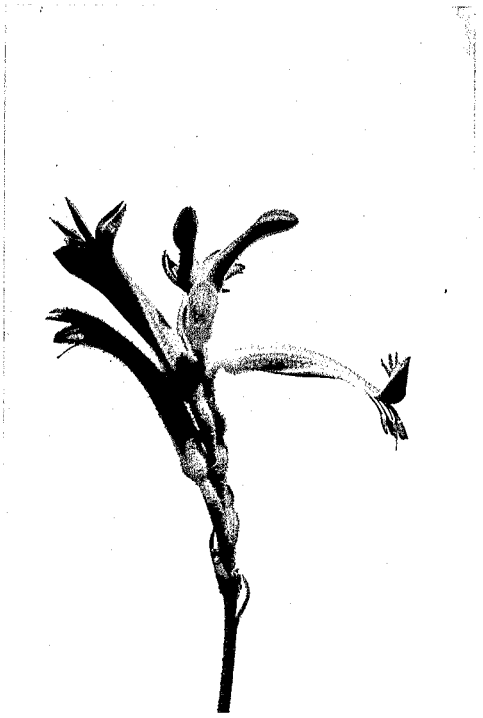

* * * * *